United States Patent [19]

Steppe

[11] Patent Number: 5,217,465

[45] Date of Patent: Jun. 8, 1993

[54] FLEXIBLE AND STEERABLE ASPIRATION TIP FOR MICROSURGERY

[75] Inventor: Dennis L. Steppe, Anaheim, Calif.

[73] Assignee: Alcon Surgical, Inc., Fort Worth, Tex.

[21] Appl. No.: 841,990

[22] Filed: Feb. 28, 1992

[51] Int. Cl.$^5$ ............... A61B 17/00; A61M 1/00
[52] U.S. Cl. ................... 606/107; 606/1; 604/19; 604/27; 604/35; 604/95; 604/281; 604/902
[58] Field of Search ............ 606/1, 107; 623/4, 6; 604/35, 95, 281, 902, 19, 27

[56] References Cited

U.S. PATENT DOCUMENTS

| | | |
|---|---|---|
| 1,741,740 | 12/1929 | Sederholm et al. |
| 3,757,768 | 9/1973 | Kline ........................... 604/95 |
| 3,847,154 | 11/1974 | Nordin . |
| 3,856,009 | 12/1974 | Winnie .......................... 604/281 |
| 3,994,297 | 11/1976 | Kopf ............................ 606/107 |
| 4,169,984 | 10/1979 | Parisi . |
| 4,210,146 | 7/1980 | Banko . |
| 4,445,509 | 5/1984 | Auth . |
| 4,473,077 | 9/1984 | Noiles et al. |
| 4,672,964 | 6/1987 | Dee et al. |
| 4,764,165 | 8/1988 | Reimels et al. ............... 604/35 |
| 4,787,399 | 11/1988 | Bonello et al. ............... 604/95 |
| 4,909,249 | 3/1990 | Akkas et al. ................. 606/107 |
| 5,084,012 | 1/1992 | Kelman . |
| 5,112,339 | 5/1992 | Zelman ......................... 606/107 |
| 5,123,840 | 6/1992 | Nates ........................... 604/902 |

FOREIGN PATENT DOCUMENTS

| | | | |
|---|---|---|---|
| 57321 | 1/1975 | Australia . | |
| 43-27685 | 11/1968 | Japan .......................... 604/95 |
| 0156901 | 11/1956 | Sweden ........................ 604/95 |
| 992044 | 2/1983 | U.S.S.R. . | |
| 203230 | 10/1983 | U.S.S.R. . | |
| 1572614 | 6/1990 | U.S.S.R. ...................... 606/107 |

OTHER PUBLICATIONS

G. A. Smith, Preliminary Report on a New Method of Intestinal Intubation with the Lid of a Flexible Stylet with Controllable Tip-Surgery, vol. 27, No. 6, Jun. 1950, pp. 817–821.
USCI Catalog—p. 6, 1967.
Oasis Product Catalog, pp. 1, 2 and 8, 1991.
Visitec Product Catalog, pp. 1–25, 1990.

Primary Examiner—Stephen C. Pellegrino
Assistant Examiner—Glenn Dawson
Attorney, Agent, or Firm—Sally Yeager; Jeffrey S. Schira

[57] ABSTRACT

A flexible and steerable aspiration tip for microsurgery includes a tip portion, the configuration of which may be remotely altered to access different areas at a surgical site. The aspiration tip includes a flexible portion which includes a spring material therewith which may be configured in a relaxed and pre-curved state or, alternatively, a stressed and straight configuration. The aspiration tip may be combined with a handpiece assembly which includes means to remotely alter the configuration of the aspiration tip. Different surgical procedures can be formed with a single flexible and steerable aspiration tip which results in a reduction of trauma and stress to the surgical site by elimination of the use of several surgical instruments and complicated surgical techniques.

10 Claims, 7 Drawing Sheets

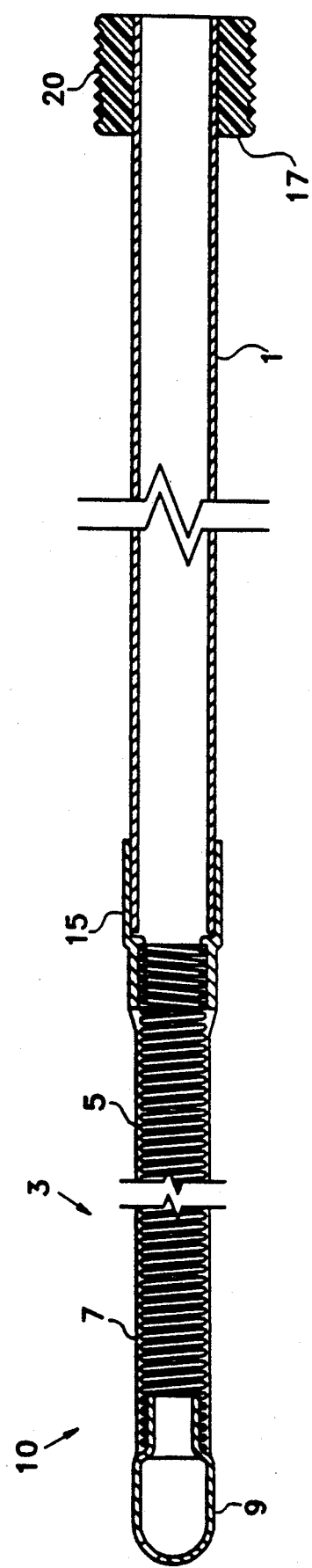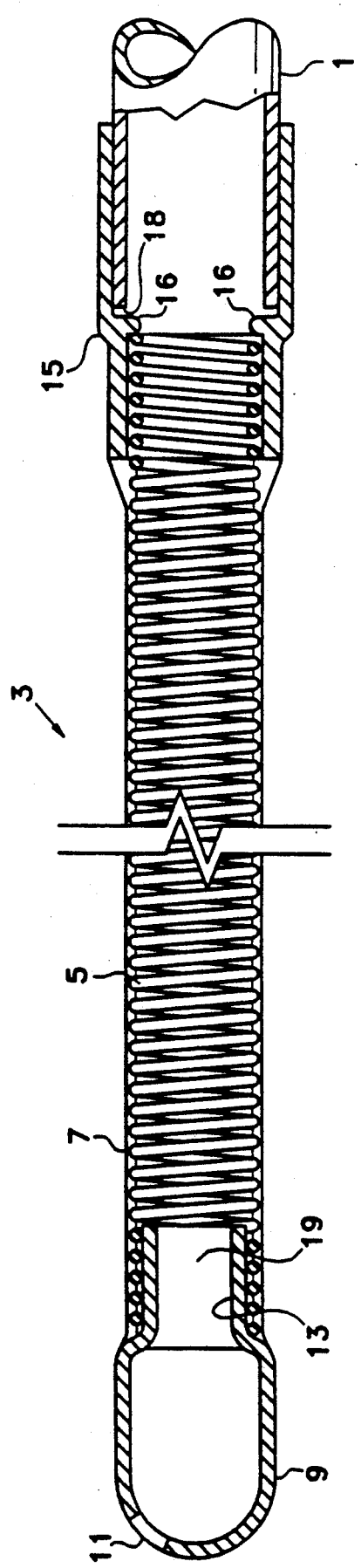
FIG. 3
FIG. 4

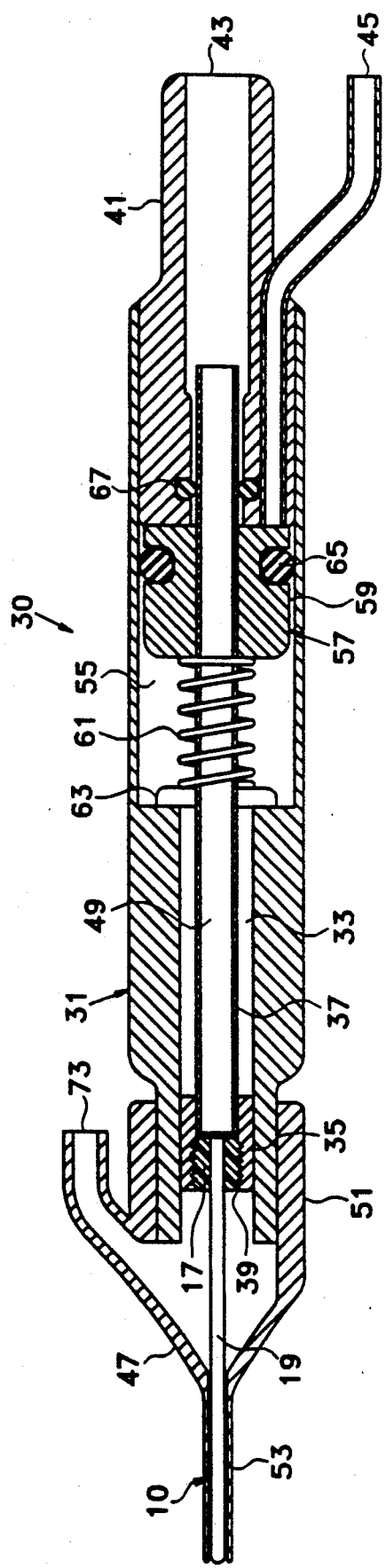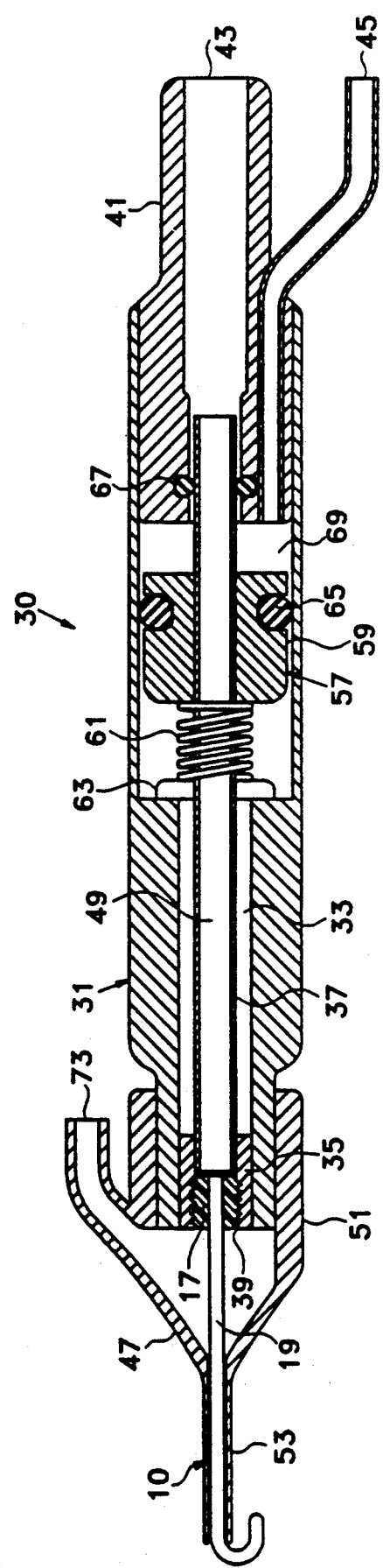
FIG. 6
FIG. 7

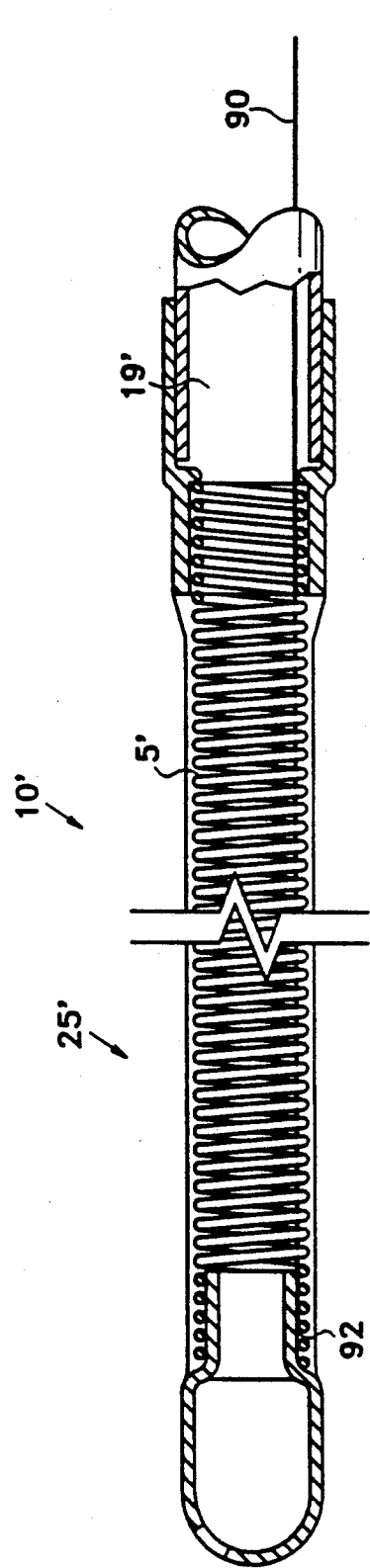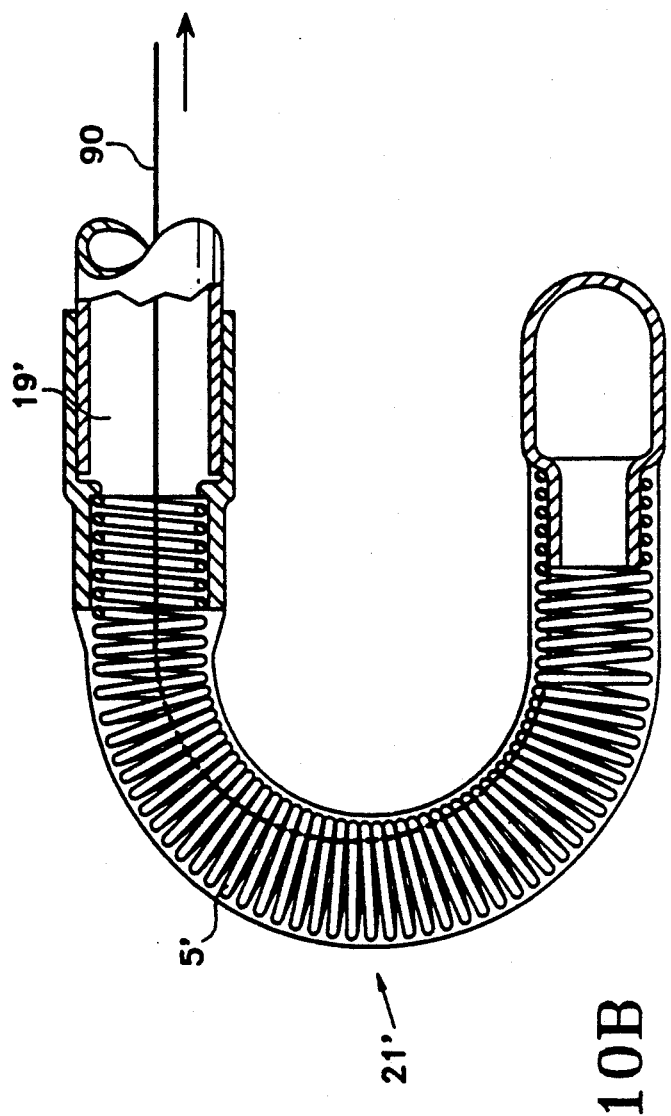
FIG. 10A
FIG. 10B

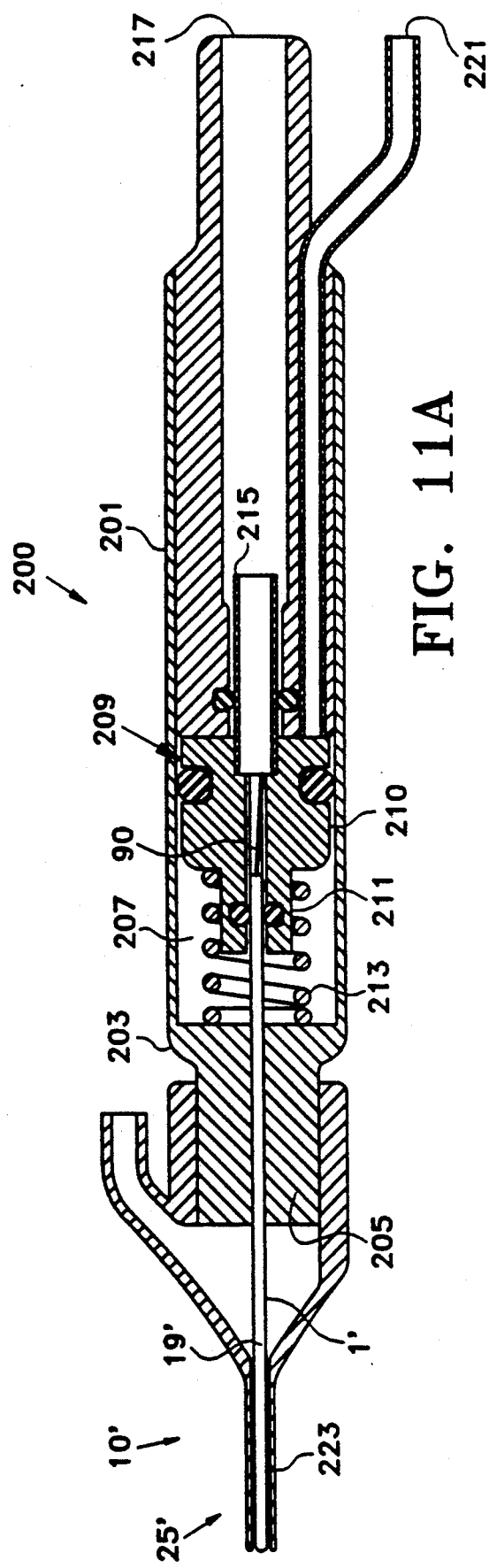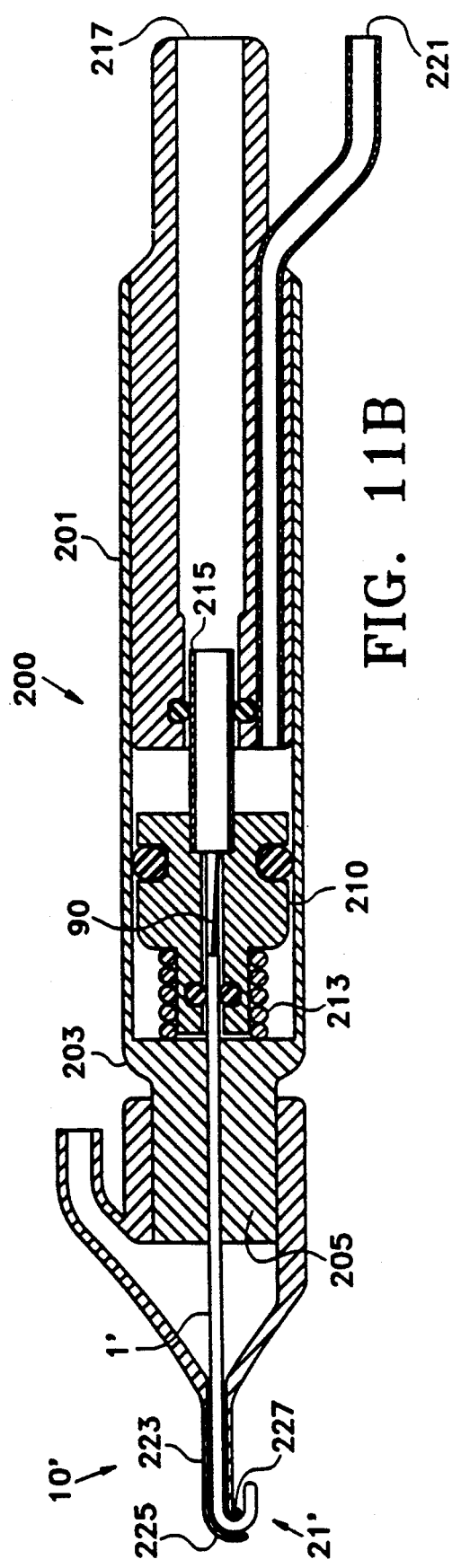

FLEXIBLE AND STEERABLE ASPIRATION TIP FOR MICROSURGERY

FIELD OF THE INVENTION

The present invention is directed to a flexible and steerable aspiration tip for microsurgery. The flexible and steerable aspiration tip includes a flexible tip portion, the shape of which may be remotely altered to permit the tip portion to access difficult to reach areas while performing a variety of surgical procedures. The flexible and steerable aspiration tip is especially adapted for microsurgical procedures in the field of surgery, such as ophthalmic surgery including cataract extraction and neuro or ear surgery.

BACKGROUND ART

In the prior art, numerous devices having angled or movable portions have been proposed to facilitate device manipulation in various medical procedures. U.S. Pat. No. 4,169,984 to Parisi discloses an ultrasonic probe assembly for use in surgical procedures. The ultrasonic probe includes an angled tip portion as best seen in FIG. 2. However, the tip of Parisi does not include structure to permit movement thereof during surgical procedures.

U.S. Pat. No. 4,210,146 to Banko discloses a surgical instrument with a bendable blade. The blade is designed to move with respect to an opening in the instrument tip to make a shearing action to cut tissue which enters the opening. The blade is formed in a manner so that, as it reciprocates into a tapered portion of the distal end tube, it will bend to conform to the shape of the tapered portion of the tube to provide continuous contact and improve cutting action. The surgical instrument of Banko does not teach or suggest a flexible tip the shape of which may be remotely altered to access different surgical sites.

U.S. Pat. No. 4,445,509 to Auth discloses a rotating cutting tool having spirally shaped cutting flutes with different cutting properties. The tool is driven from outside the tool body by means of a flexible drive shaft. The tool of Auth is designed to be inserted into a human vascular network to remove plaque deposits.

U.S. Pat. No. 4,473,077 to Noiles et al. discloses a surgical stapler apparatus having a flexible shaft. The apparatus includes structure which greatly reduces or essentially eliminates the tendency of the shaft assembly to revert to its straight condition during transmittal of longitudinal forces during stapling.

U.S. Pat. No. 4,672,964 to Dee et al. discloses a scalpel having a universally adjustable blade mounted to the scalpel handle for selective positioning. The scalpel includes structure which permits rotation of the blade about the axis of the handle as well as angular positioning with respect thereto. However, the scalpel assembly does not include means which permits flexing or bending of the scalpel or scalpel assembly during use.

U.S. Pat. No. 3,847,154 to Nordin discloses a surgical drill having an angular housing which is particularly useful where it is desired to reach very inaccessible areas in the body during a sensitive operation. However, the angular housing of the surgical drill disclosed in the Nordin patent is not flexible or adjustable.

Australian Patent Specification Number 57321 to Pericic discloses an oscillating surgical knife which has specific applications to eye surgery. The oscillating surgical knife, in one embodiment, includes a chuck which permits angular displacement of the blade in the direction of oscillation thereby allowing the blade to be located at angles to enable the blade to reach a position which may otherwise be difficult or impossible. However, the oscillating surgical knife of Pericic does not include structure or means to permit the knife to be flexibly steered to access difficult to reach areas.

U.S. Pat. No. 1,741,740 to Sederholm et al., Soviet Union Patent Number 992044 to Crimea Medical Institute and East German Patent Number 203,230 to Streubel disclose surgical cutting instruments having adjustable blades therewith. None of these documents disclose a flexible and steerable aspiration tip for use in microsurgery.

In the field of cataract surgery, the goal of the surgery is the removal and anatomical replacement of an original, clouded lens with an optically clear intraocular lens using a small incision as well as a minimum of trauma to the surgical site. Current techniques being used to effect cataract surgery include extra capsular cataract extraction (ECCE) or endocapsular phacoemulsification (ECPE). As part of these techniques, a small gauge irrigation/aspiration tip is used to remove any residual cortex and epithelium adjacent the capsular bag.

With reference to FIGS. 1 and 2, examples of cataract surgery techniques are depicted to illustrate deficiencies in prior art surgical instruments. FIG. 1 illustrates a sectional view of an eye 100 including a cornea 103, sclera 105, iris 107 and capsular bag 111. During extracapsular cataract extraction, a straight and rigid irrigation/aspiration instrument 113 having a tip portion 115 is inserted into the eye through the limbal incision 117. Peripheral cortex is easily engaged by the irrigation/aspiration tip 115 at the location directly opposite the incision designated by reference numeral 119. However, as can be seen in FIG. 1, the cortex directly under the iris 107 directly below the incision 121 is difficult to access when using a straight and rigid irrigation/aspiration tip.

In an effort to remove the cortex from the location directly below the incision, several complicated and difficult manuevers using the straight and rigid irrigation/aspiration tip must be employed. In one manuever, the iris is drawn out of the wound using smooth forceps while the irrigation/aspiration tip is inserted and exposed cortex is engaged by aspiration. These manuevers are difficult to execute since visualization of the underlying cortex through the iris is impossible and, in certain cases with a constricted iris, even more difficult to perform. As a result of these different manuevers, excess trauma may result in the surrounding ocular tissue including exposing and/or weakening of the zonules 120, or enlargement of the limbal incision with subsequent possible collapse of the anterior chamber 109.

In response to these deficiencies in the prior art, irrigation/aspiration tips have been proposed having an angled or bent configuration. With reference now to FIG. 2, an irrigation/aspiration tip 123 is shown inserted through the limbal incision 117 and including an angled tip portion 125. Using the angled tip 125, cortex may be easily removed from the 12 o'clock position 121. However, engagement and removal of cortex directly under the iris at the 6 o'clock position 119 becomes difficult using the angled tip 125.

To achieve cortex removal from both the 6 o'clock position 119 and the 12 o'clock position 121, both the straight and rigid irrigation/aspiration tip 113 and the angled tip 123 must be used during the surgical procedure. Using both surgical instruments requires removal of one followed by insertion of the other which results in additional trauma to the surrounding ocular tissue during the surgical operation as well as requiring additional items for each surgical procedure with the attendant sterilization, cleanliness and assembly requirements.

These techniques are also applicable to endocapsular cataract extraction wherein the capsular bag is left relatively intact and the irrigation/aspiration tip is introduced via a small limbal incision and a small anterior capsulotomy.

In response to these deficiencies in prior art instruments, a need has developed to provide a single surgical instrument which permits access to difficult to reach areas while still performing a desired surgical procedure such as aspiration of cortex or other lenticular material during a cataract extraction operation.

In response to this need, the present invention provides a flexible and steerable aspiration tip for microsurgery, in particular, ophthalmic surgery such as cataract removal. The flexible and steerable aspiration tip of the present invention includes a flexible tip portion, the shape of which may be remotely altered to permit the tip portion to access difficult to reach areas. The flexible and steerable aspiration tip permits performing a variety of surgical procedures while eliminating the requirement of using differently configured tips during the surgical procedure.

None of the prior art cited above teaches or fairly suggests a flexible and steerable aspiration tip including means to remotely position the flexible tip portion to access hard to reach areas.

SUMMARY OF THE INVENTION

It is according a first object of the present invention to provide a flexible and steerable aspiration tip for microsurgery.

It is a further object of the present invention to provide a flexible and steerable aspiration tip which includes an aspiration tip having a flexible portion and means to remotely flex and position the aspirating tip to access difficult to reach areas during microsurgical procedures.

It is a further object of the present invention to provide a flexible and steerable aspiration tip which is especially adapted for cataract extraction procedure wherein any lenticular material, for example, nuclear, capsular or cortical material, may be removed using one instrument while simultaneously minimizing trauma to adjacent intraocular tissue sites.

It, is a still further object of the present invention to provide a flexible and steerable aspiration tip for removing softened lenticular material during cataract surgical procedures which results in a minimum of stress and avoidance of tearing and/or rupturing of the lens capsule and/or zonules using a single instrument.

It is a yet further object of the present invention to provide a flexible and steerable aspiration tip for microsurgery which includes a tip portion in combination with a handpiece, the handpiece including structure to facilitate remotely flexing and steering the tip portion in numerous configurations.

In satisfaction of the foregoing objects and advantages, there is provided a flexible and steerable aspiration tip for microsurgery, in particular, cataract extraction procedures. The flexible and steerable aspiration tip for microsurgery includes a tip portion comprising a straight rigid portion, a flexible portion and a spherical distal cap. The flexible portion further includes a prestressed activation spring coated by an elastomeric material, the spring having a curved shape in its relaxed state. The flexible portion is disposed and coupled between the distal cap and straight rigid portion.

In a preferred embodiment, the flexible and steerable aspiration tip includes a handpiece assembly which includes a housing adapted to provide aspiration therethrough, a piston assembly and sleeve. The piston assembly and sleeve cooperate with the flexible portion to provide flexing and steering of the tip during a surgical or medical procedure such as cataract extraction.

The aspiration tip is designed to removably attach to the handpiece and connect to the piston assembly. The piston assembly longitudinally translates the aspirating tip within the rigid sleeve. By retracting the flexible portion of the tip within the rigid sleeve, the energy of the activation spring is overcome such that the spring and flexible tip are configured in a straight and rigid manner. In this mode, the aspiration tip is in a straight and rigid configuration for use in cataract surgery. By extending the flexible portion of the tip outside the confines of the sleeve, the spring is permitted to return to its relaxed state such that the tip is configured in a curved manner to access difficult to reach areas in the surgical site.

The sleeve is designed to engage an outer and distal end of the handpiece and includes a passageway to provide irrigation fluid to the surgical site. The sleeve includes a rigid tubular distal end which maintains the activation spring in its straight configuration when the piston assembly retracts the aspiration tip within the sleeve.

In another embodiment, the flexible and steerable aspiration tip includes a handpiece assembly which includes a housing adapted to provide aspiration therethrough, a piston assembly and sleeve. A pull wire attached to the distal end of the flexible and steerable aspiration tip and the piston assembly provides the flexing and steering of the tip during a surgical or medical procedure such as cataract extraction. This embodiment allows the use of a soft, elastomeric sleeve to surround the flexible and steerable aspiration tip to provide for irrigation to the surgical site. Also, this embodiment allows the flexible and steerable aspiration tip to be used without a sleeve.

BRIEF DESCRIPTION OF THE DRAWINGS

Reference is now made to the Drawings accompanying the application wherein:

FIG. 3 shows a longitudinal sectional view of the aspiration tip of the flexible and steerable aspiration tip of the present invention;

FIG. 4 shows the distal end of the aspiration tip depicted in FIG. 3 enlarged to show greater detail;

FIG. 6 shows a longitudinal sectional view of an irrigation/aspiration handpiece utilizing the aspiration tip depicted in FIG. 1;

FIG. 7 shows a longitudinal sectional view of the irrigation/aspiration handpiece depicted in FIG. 6 with the flexible and steerable aspiration tip in the curved configuration;

FIGS. 10A and 10B show another embodiment of the flexible and steerable aspiration tip; and FIGS. 11A and 11B show a longitudinal sectional view of the irrigation/aspiration handpiece using the aspiration tip depicted in FIGS. 10A and 10B.

DESCRIPTION OF THE PREFERRED EMBODIMENTS

Figure 1:
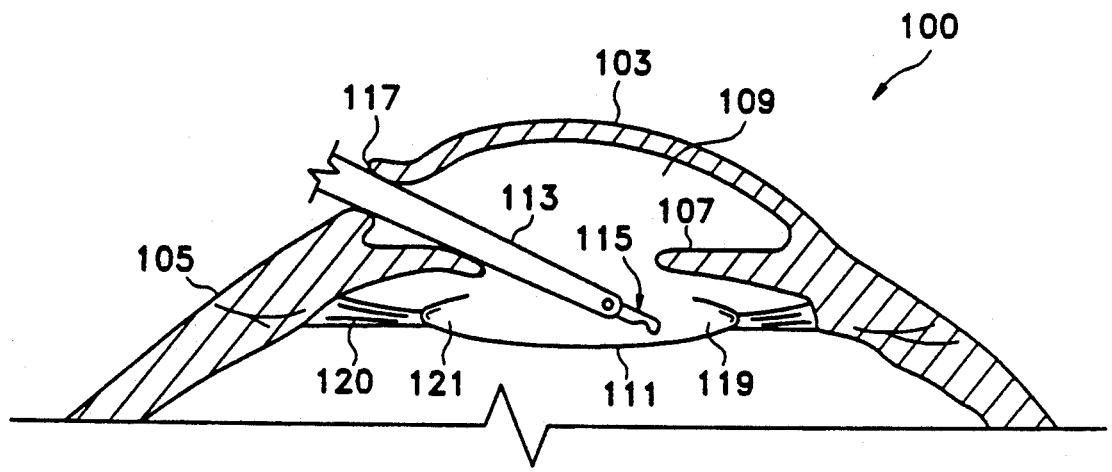
FIG. 1 shows a schematic view of a prior art irrigation/aspiration tip in an exemplary cataract extraction procedure.
Figure 2:
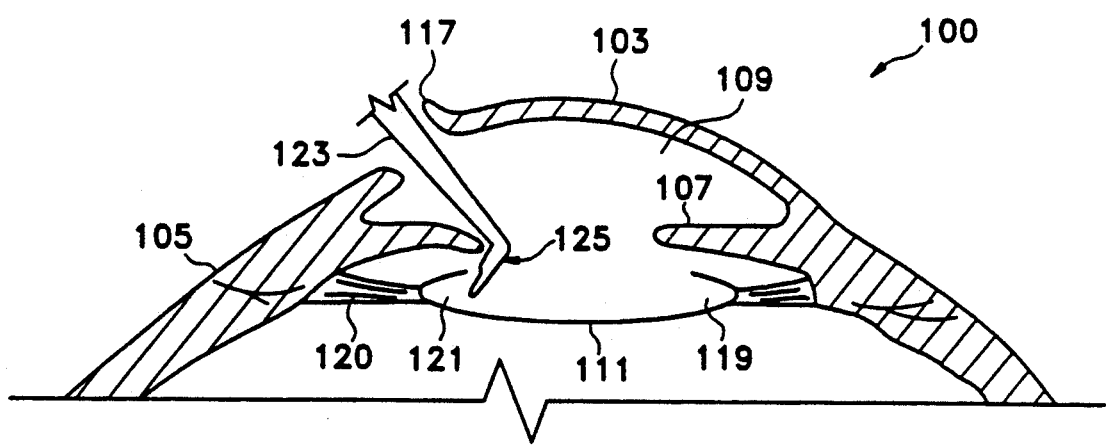
FIG. 2 shows another prior art irrigation/aspiration tip in an exemplary cataract extraction procedure.

The present invention is concerned with a flexible and steerable aspiration tip for microsurgery, particularly for use in surgical procedures in the field of ophthalmic surgery. The flexible and steerable aspiration tip of the present invention offers advantages over prior art devices by eliminating the necessity of using a plurality of instruments to perform surgical procedures such as in, for example, cataract extraction. By using a single instrument to remove cortical lenticular tissue in a cataract extraction surgical procedure, trauma to surrounding intraocular structures caused by withdrawal and reinsertion of a plurality of instruments is significantly reduced. In addition, the flexible and steerable aspiration tip permits removal of softened lenticular material without causing stress and possible consequent tearing and/or rupturing of lens capsules and/or zonules.

Although the flexible and steerable tip has been disclosed for use in cataract extraction procedures, the flexible tip may be adapted for use as a bendable irrigating cannula or illuminator in ophthalmic surgical procedures involving the posterior segment of the eye as in vitreous and/or retinal surgery as well as in other microsurgical disciplines such as neuro- or ear surgery.

The flexible and steerable aspiration tip, in one embodiment, may be coupled with an irrigation/aspiration handpiece to permit manipulation of the aspiration tip at a surgical site as well as provide a means for remotely altering the configuration of the distal end of the flexible and steerable tip.

With reference now to FIGS. 3 and 4, the flexible and steerable aspiration tip is generally designated by the reference numeral 10 and is seen to include a rigid tubular member 1. The rigid tubular member 1 may be made out of a suitable sized, stainless steel, thin-walled hypodermic tubing. The aspiration tip 10 also includes a flexible portion 3 which comprises an activation spring 5 covered by a thin layer of elastomeric material 7. Adjacent the distal end of the flexible portion 3 is a spherical distal cap 9 having an aperture 11 at the distal end thereof. The distal cap 9 is generally hollow and may be manufactured of stainless steel by progressive die or cold forming processes. The aperture 11 may be formed in the distal cap 9 by drilling, bead blasting or other known processes. Alternatively, the tubular member 1 and distal cap may be made from polymeric materials such as thermoplastics, e.g. ABS, polycarbonate, polypropylene or the like.

The distal cap 9 includes a hollow male end 13 which is designed to be inserted within the spring 5 to couple the distal cap 9 to the flexible portion 3. The flexible portion 3 is coupled to the rigid tubular member 1 via the coupling 15. As can be seen from FIG. 4, the coupling 15 is designed to receive the proximal end of the spring 5 and the distal end of the tubular member 1. The coupling 15 also includes a lip 16 designed to engage the distal end face 18 of the tubular member 1. The coupling 15 may also be made out of a stainless steel material. The spring 5, coupling 15 and tubular member 1 may be permanently joined by well known processes such as electrobeam welding.

The tubular member 1 also includes a metal or plastic hub 17 having external threads 20 thereon. The hub 17 may be press fit or attached in other known manners to the tubular member 1. The hub is designed to facilitate attachment of the aspiration tip 10 to a suitable handpiece as will be discussed hereinafter.

With reference now to FIG. 4 again, the thin elastomeric material 7 may be a polymer such as polyolefin or fluorosilicon. The elastomeric material 7 isolates the internal lumen 19 from the surrounding environment. Coating of the elastomeric material 7 on the spring 5 may be accomplished by a known processes such as injection insert molding, utilizing an internal mandrel in order to straighten the spring material during the overmolding process as well as keeping the lumen 19 of the aspiration tip open. The internal mandrel would be subsequently removed after the overmolding process completes coating of the spring material.

Figure 5:
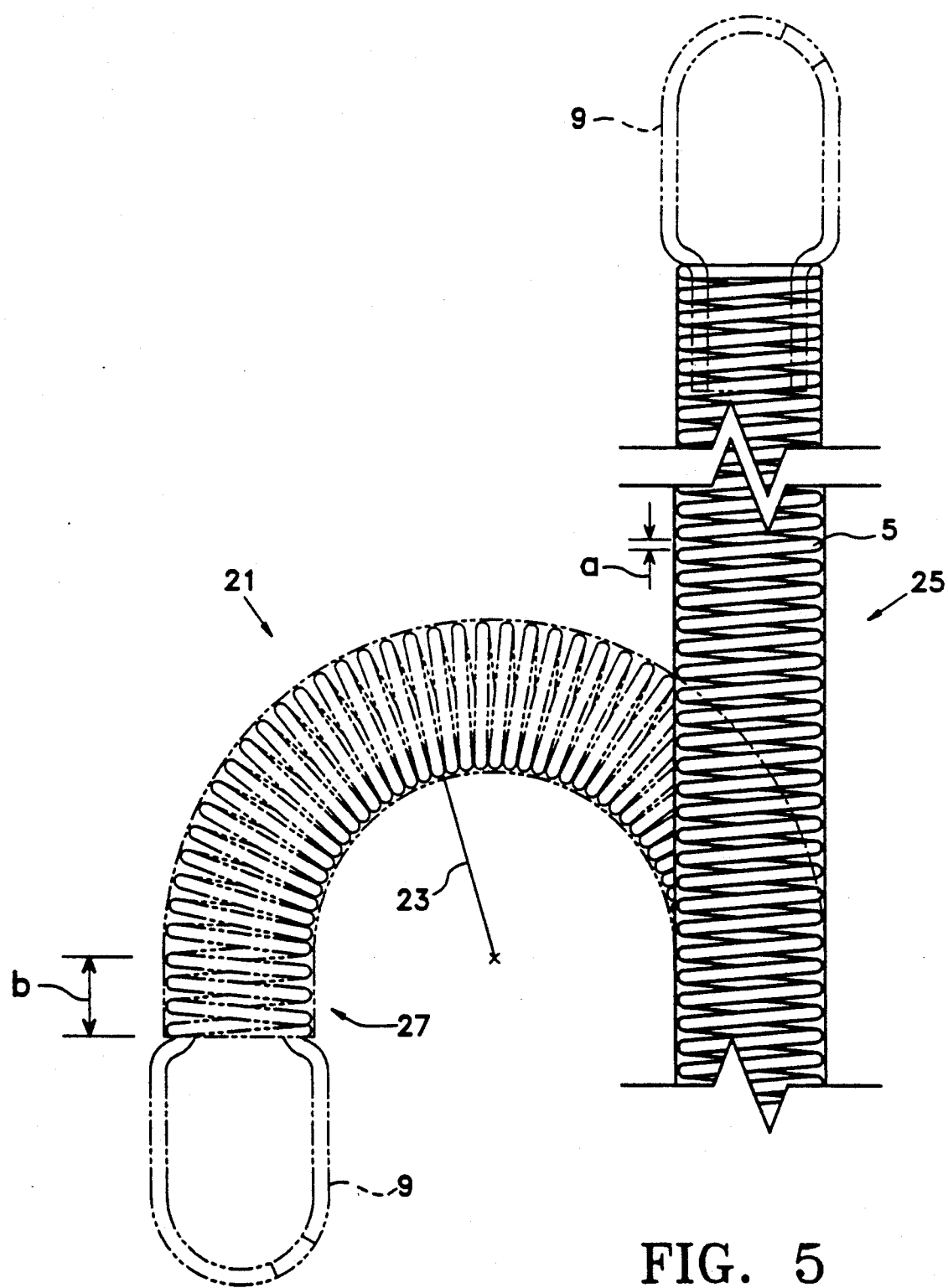
FIG. 5 shows a portion of the aspiration tip showing the spring in a relaxed and a stressed state.

FIG. 5 shows a schematic representation of the spring 5 in both the pre-curved or relaxed state and the straight, stressed state. As can be seen from FIG. 5, the curved or relaxed state is designated by the reference numeral 21 with the straight and stressed state designated by the reference numeral 25. The relaxed state 21 includes a defined radius designated by the reference numeral 23. In the relaxed state, the spring material includes on the distal end thereof a portion 27 having a length b. This straight portion 27 is designed to receive the distal cap 9 shown in cross-hatch. It should be understood that the activation spring 5 is manufactured from a material such as stainless steel wire in a relaxed state having the curve shown in FIG. 5. The process to manufacture these types of stainless steel springs having pre-curved configuration are well recognized in the prior art, as such, not considered an aspect of the present invention. A typical spring would include an outer diameter of 0.04 inches and an overall length of 0.31 inches. A typical radius of curvature would be 0.04 inches with the number of activation coils numbering 42 and the wire diameter as well as spacing between coils approximately 0.003 inches. As will be described hereinafter, the activation spring 5 may be straightened to the stressed state 25 by application of a force greater than the energy of the spring in the relaxed state 21.

With reference now to FIGS. 6 and 7, the flexible and steerable aspiration tip is shown in combination with an exemplary handpiece, the handpiece being designated by the reference numeral 30. The handpiece 30 comprises a hollow housing 31 which is generally cylindrical in shape and of a length which approximates the length of a pencil to facilitate being held by a user. The housing 31 includes a bore 33 therein. Disposed within the bore 33 are an insert 35 and a length of rigid tubing 37. The insert 35 has an opening 39 which allows attachment of the aspiration tip 10 to the insert 35 by the hub 17 threadably engaging the internal threads (not shown) within the opening 39 of the insert. The rigid tube 37 may be integrally attached to the insert 35 so as to maintain the lumen passageway 19 along the lumen 49 within the rigid tubing 37. Other known coupling techniques may be utilized to provide removable attachment between the tip and handpiece components as well as between handpiece components, such press fitting, use of fasteners or the like.

The distal end of the housing 31 of the handpiece 30 is designed to accept a cap 47. The cap 47 comprises a sleeve portion 51 which is designed to engage the outer surface of the housing 31 at the distal end thereof for attachment purposes. The cap 47 includes a thin-walled rigid sleeve 53. The thin-walled rigid sleeve may be of the type disclosed in U.S. Pat. No. 4,787,899 to Steppe et al., which is herein incorporated by reference. The proximal end of the housing includes end cap 41 having ports 43 and 45.

The housing 31 of the handpiece 30 includes a chamber 55 which contains a piston assembly 57. The piston assembly 57 includes a piston 59, a spring 61, bulkhead 63 and O-ring 65. The end cap 41 also includes an O-ring 67 at the distal end thereof.

It should be understood that FIG. 6 illustrates the handpiece 30 in a rest state with the flexible and steerable aspiration tip in a stressed state. With reference now to FIG. 7, the handpiece 30 is shown in the fully compressed state with the aspiration tip 10 shown in the fully relaxed state with the flexible portion in the curved position. In achieving the compressed state depicted in FIG. 7, pneumatic pressure is applied through the port 45 against the piston 59. The pneumatic pressure causes the piston 59 to move toward the distal end of the handpiece to compress the spring 61 against the bulkhead 63. Since the piston is attached to the tubular member 37, insert 35 and aspiration tip 10, longitudinal movement of the piston along the axis of the handpiece translates to longitudinal movement of the aspiration tip 10. O-rings 65 and 67 seal the chamber 69 between the piston 59 and the end cap 41 to permit application of pneumatic pressure against the piston. By moving the aspiration tip 10 past the inner circumference of the rigid sleeve 53, the external force which acts to straighten the flexible portion 3 of the aspiration tip 10 is relieved. As a result, the flexible portion 3 of the tip, when extended beyond the distal end of the rigid sleeve 53 is permitted to return to its relaxed and curved state. By relieving the pneumatic pressure through the port 45, the spring 61 returns to its rest state, thereby translating the piston 59 toward the proximal end of the handpiece 30 and retracting the aspiration tip 10 within the sleeve 53. Relieving the pneumatic pressure results in the aspiration tip obtaining a straight configuration by confining the flexible portion 3 within the rigid sleeve 53 to overcome the energy of the spring 5. Although a piston assembly is used to provide a means to translate the tip between stressed and relaxed states, other means such as bellows or a diaphragm driven by pneumatic power may be utilized. Another alternative would be an electrically driven motor and cam assembly.

The cap 47 also includes a port 73 which may be used to supply irrigation fluid to the surgical site. The irrigation fluid would flow through the port 73 and between the aspiration tip 10 and inner circumference of the rigid sleeve 53 exiting at the distal end thereof. Of course, the distal end of the rigid sleeve 53 may have one or more apertures therein to facilitate flow of irrigation fluid therefrom.

The three ports, 43, 45 and 73 of the handpiece 30 are connected to a control unit. Although not shown, the control unit is designed to control flow of irrigation fluid to the handpiece, aspiration from the handpiece, and application of pneumatic pressure by a user of the inventive device. It should be understood that these types of control units are well recognized in the field of surgical aspiration and irrigation instrumentation and, therefore, are not described in greater detail.

Figure 8A:
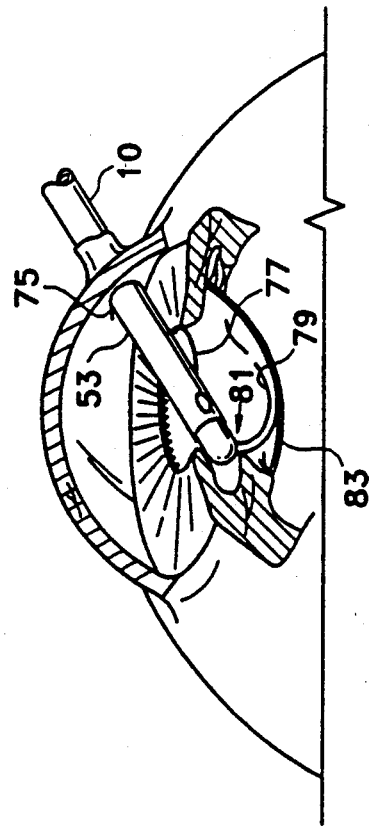
FIGS. 8A and 8B show a diagrammatical cross-section of a human eye during a cataract extraction surgical procedure utilizing the inventive flexible and steerable aspiration tip.
Figure 8B:
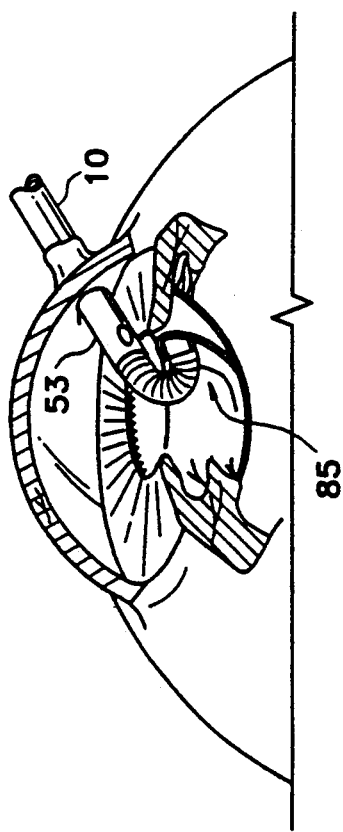

With reference now to FIG. 8A and 8B, an exemplary use of the flexible and steerable aspiration tip are illustrated. With reference to FIG. 8A, the aspiration tip 10 is depicted during a typical cortical clean-up phase of a planned extracapsular cataract extraction or phacoemulsification cataract surgery. The aspiration tip 10 and sleeve 53 are shown inserted through a limbal incision 75 and anterior capsulotomy 77 to remove cortical material 79 at the location designated by the reference numeral 81. As can be seen, the flexible and steerable aspiration tip is in the straight configuration to readily engage, strip the underlying cortex from the lens capsule 83 and aspirate removed material.

With reference to FIG. 8B, pneumatic pressure is applied to the handpiece (not shown) to extend the flexible and steerable aspiration tip 10 from the confines of the sleeve 53 to achieve the curved configuration. In this manner, the curved tip may access the cortical material at the location designated by the reference numeral 85. During this procedure, it should be noted that the surgical instrument is not required to be removed from the surgical site to access all cortical material in the lens capsule 83.

Figure 9A:
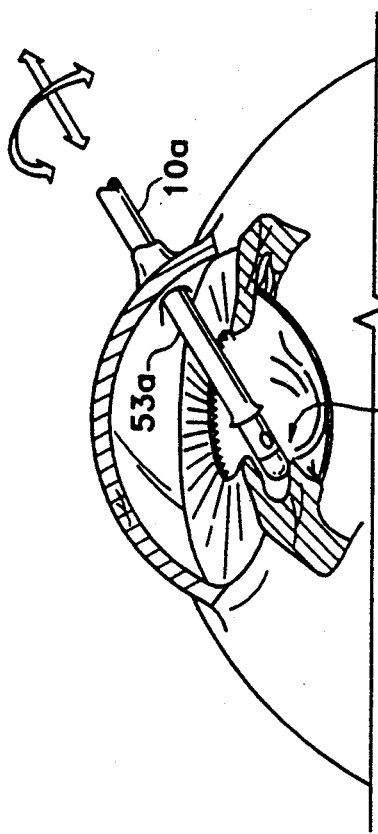
FIGS. 9A and 9B show a diagrammatical cross-section of a human eye during another type of cataract surgical procedure utilizing the inventive flexible and steerable aspiration tip.
Figure 9B:
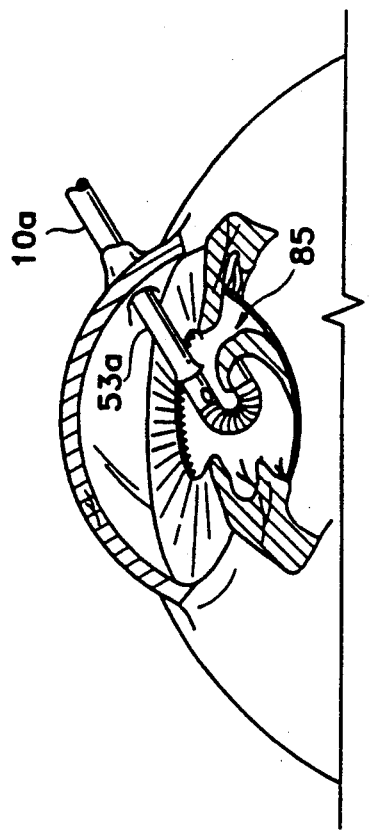

FIGS. 9A and 9B illustrate another exemplary use of the flexible and steerable aspiration tip in a endocapsular cataract surgical procedure wherein a small anterior capsulotomy is performed such that the endocapsular bag remains essentially intact. FIGS. 9A and 9B also illustrate a flexible and steerable aspiration tip 10a and sleeve 53a of slightly smaller diameter than that disclosed in FIGS. 8A and 8B. Again, by remotely controlling the configuration of the distal end of the flexible and steerable aspiration tip 10a, lenticular material may be removed from both the location 81 as well as the location 85. FIG. 9A also illustrates that the flexible and steerable aspiration tip 10a may be rotated to position the aperture in the distal cap of the flexible tip in a desired location. Thus, using the curved configuration of the flexible and steerable aspiration tip allows a wide degree of coverage by the aspiration port. Again, the flexible and steerable aspiration tip 10a can replace several instruments to perform the same surgical procedure and minimize trauma to the intraocular surgical site such as capsule tearing or zonular rupture. In addition, trauma to intraocular areas such as the iris or zonules are also minimized by using a single instrument having ready access to all capsular positions.

Another embodiment of a flexible and steerable aspiration tip is shown in FIGS. 10A and 10B. In this embodiment, a spring 5', which is similar to the spring disclosed in FIG. 5, is provided with a pull wire 90 extending therethrough. The pull wire 90 is attached to the distal end of the spring 5' at reference numeral 92. The pull wire 90 extends through the lumen 19' and into the irrigation/aspiration handpiece as will be described hereinafter. The spring 5' includes a similar configuration as described for the spring 5 in FIG. 5 and includes a relaxed state 21' and a stressed state 25'. The pull wire may be made of many materials and dimensions, with a preferred material being stainless steel and preferred dimensions including 0.002 inches by 0.006 inches. The pull wire 90 may be attached to the distal end of the spring 5' using any known joining techniques such as soldering, welding or the like.

With reference now to FIGS. 11A and 11B, manipulation of the aspiration tip will be described in conjunction with the embodiment depicted in FIGS. 10A and 10B. In this embodiment, an irrigation/aspiration handpiece is generally designated by the reference numeral 200 and seen to include a housing 201 having a shoulder 203 and a distal end portion of reduced diameter 205. The housing 201 includes a chamber 207 which houses a piston assembly 209.

The piston assembly 209 includes a piston 210 having a reduced diameter neck portion 211 and a spring 213 designed to engage the neck portion 211 of the piston 210. Also provided is a sleeve 215 which is mounted in the proximal end of the piston 210. The sleeve 215 maintains a channel between the lumen 19' in the flexible and steerable aspiration tip 10' and the rigid tubular member 1' and the aspiration port 217. The pull wire 90 is rigidly mounted to the piston 210.

In this embodiment, the tubular member 1' is mounted within the portion 205 of the housing 201. As such, no longitudinal translation occurs for the tubular housing 1' as is the case in the embodiment depicted in FIGS. 6 and 7 of the invention.

By movement of the piston 210 and pull wire 90, the flexible and steerable aspiration tip 10' may be configured between the straight and stressed state as depicted in FIG. 11A and the relaxed and curved state depicted in FIG. 11B. In FIG. 11A, the piston 210 is under the force of the spring 213 thereby applying a force against the pull wire 90 and straightening the aspiration tip 10'. With reference now to FIG. 11B, a pneumatic pressure is applied through the port 221 forcing the piston 210 to compress the spring 213 and relax the tension on the pull wire 90. In this condition, the aspiration tip 10' is allowed to relax to its curved position. By selectively controlling the amount of pneumatic pressure applied to the piston 210, the flexible and steerable aspiration tip 10' may be configured in any position between the straight position depicted in FIG. 11A and the fully curved position depicted in FIG. 11B.

It should be noted that, using this embodiment, a flexible sleeve 223 may be utilized in place of the rigid sleeve 53 disclosed in the embodiment depicted in FIGS. 6 and 7. Since the pull wire 90 provides the force necessary to vary the curvature of the flexible and steerable aspiration tip 10', a rigid sleeve is not required. However, since the aspiration tip 10' does not longitudinally translate within the rigid sleeve 53 as depicted in FIGS. 6 and 7, the rigid sleeve 223 will stretch on the outside curve thereof as shown by reference numeral 225 in FIG. 11B and compress on the inside curve as shown by reference numeral 227. As a result of this stretching and compressing, and the small gauge of the irrigation lumen, pumped over gravity feed, irrigation is preferable in order to achieve and maintain proper irrigation flow and velocity.

It should be understood, that the flexible and steerable aspiration tip may be combined with other types of handpieces having means similar to that shown for the handpiece 30 to extend or retract the flexible and steerable tip to achieve the desired configuration at the distal end thereof. In addition, the distal end tip may include illumination means or utilized merely for irrigation purposes alone. Furthermore, the sleeve 53 may be utilized to provide a rigid support against the flexible and steerable aspiration tip with separate irrigation means providing a source of irrigation fluid.

As such, an invention has been disclosed in terms of preferred embodiments thereof which fulfill each and every one of the objects of the present invention as set forth hereinabove and provides a new and improved flexible and steerable tip for microsurgery.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. An irrigation and aspiration handpiece for microsurgery, comprising:
   a) a housing;
   b) a cap having a relatively rigid sleeve with an open end and a longitudinal bore that is received on and attached to a distal end of the housing;
   c) an aspiration tip that is received on a tubular member in the housing and has a curved, hollow, flexible free end opposite the tubular member that projects down the longitudinal bore of the sleeve;
   d) an irrigation fluid flow passage coaxially located between the tip and the sleeve; and
   e) a piston attached to the tubular member adapted to reciprocate within a chamber in the housing in response to pneumatic pressure.

2. The handpiece of claim 1 wherein the flexible free end of the tip comprises a spring coated by an elastomeric material.

3. The handpiece of claim 1 wherein the cap comprises titanium.

4. The handpiece of claim 1 wherein the cap comprises stainless steel.

5. The handpiece of claim 1 wherein the cap comprises thermoplastic.

6. An irrigation and aspiration handpiece for microsurgery, comprising:
   a) a housing;
   b) a cap having a sleeve with an open end and a longitudinal bore that is received on a distal end of the housing;
   c) an aspiration tip that is received on a tubular member in the housing that projects down the longitudinal bore of the sleeve;
   d) a curved, hollow, flexible free end on the tip opposite the tubular member that projects outwardly from the open end of the sleeve;
   e) an irrigation fluid flow passage coaxially located between the tip and the sleeve; and
   f) a pull wire attached to a distal end of the free end and a piston attached to the pull wire opposite the free end, the piston adapted to reciprocate within a chamber in the housing in response to pneumatic pressure.

7. The handpiece of claim 6 wherein the flexible free end of the tip comprises a spring coated by an elastomeric material.

8. The handpiece of claim 6 wherein the cap comprises titanium.

9. The handpiece of claim 6 wherein the cap comprises stainless steel.

10. The handpiece of claim 6 wherein the cap comprises thermoplastic.

* * * * *